(12) United States Patent
Lizzi et al.

(10) Patent No.: US 6,423,007 B2
(45) Date of Patent: Jul. 23, 2002

(54) ULTRASONIC SYSTEMS AND METHODS FOR CONTRAST AGENT CONCENTRATION MEASUREMENT

(75) Inventors: Frederic Louis Lizzi, Tenafly; Cheri Xiaoyu Deng, Edison, both of NJ (US)

(73) Assignee: Riverside Research Institute, New York State ( * ) Notice: Subject to any disclaimer, the term of this patent is extended or adjusted under 35 U.S.C. 154(b) by 0 days.

(21) Appl. No.: 09/734,058

(22) Filed: Dec. 11, 2000

Related U.S. Application Data

(62) Division of application No. 09/318,882, filed on May 26, 1999, now Pat. No. 6,186,951.
(60) Provisional application No. 60/086,748, filed on May 26, 1998.

(51) Int. Cl.[7] .................................................. A61B 8/14
(52) U.S. Cl. ...................................... 600/458; 424/952
(58) Field of Search ................................. 600/437, 453, 600/454, 458, 407, 587, 594, 595, 476, 447; 424/9.52; 367/92; 250/334; 356/317

(56) References Cited

U.S. PATENT DOCUMENTS

| | | | |
|---|---|---|---|
| 4,858,124 A | | 8/1989 | Lizzi et al. |
| 4,932,414 A | | 6/1990 | Coleman et al. |
| 5,685,310 A | * | 11/1997 | Porter .......................... 600/458 |
| 5,732,707 A | * | 3/1998 | Widder et al. ............... 600/454 |
| 5,733,527 A | | 3/1998 | Schutt |
| 5,746,209 A | | 5/1998 | Yost et al. |
| 5,846,517 A | * | 12/1998 | Unger ........................ 424/9.52 |
| 5,860,931 A | * | 1/1999 | Chandler ..................... 600/458 |
| 5,976,501 A | * | 11/1999 | Jablonski .................... 424/9.52 |
| 6,110,120 A | * | 8/2000 | Holley et al. ................ 600/458 |
| 6,132,377 A | * | 10/2000 | Bolorforosh et al. ........ 600/458 |
| 6,159,153 A | | 12/2000 | Dubberstein et al. |
| 6,176,829 B1 | | 1/2001 | Vilkomerson |
| 6,193,663 B1 | * | 2/2001 | Napolitano et al. .......... 600/447 |
| 6,213,951 B1 | * | 4/2001 | Krishnan et al. ............ 600/458 |

OTHER PUBLICATIONS

Deng et al., "Imaging and Spectrum Analysis of Contrast Agents in the *In Vivo* Rabbit Eye Using Very–High–Frequency Ultrasound", Ultrasound in Med & Biol. vol. 24, No. 3, pp. 383–394, 1998.

\* cited by examiner

*Primary Examiner*—Marvin M. Lateef
*Assistant Examiner*—Ali M. Imam
(74) *Attorney, Agent, or Firm*—Baker Botts LLP

(57) ABSTRACT

The concentration and/or radii of a contrast agent in a fluid can be estimated by acquiring ultrasound spectral data, performing spectral analysis to generate a linear estimation of the power spectrum, and correlating at least one spectral parameter to a predetermined distribution function for the contrast agent. If the mean radius squared of particles is known, then the concentration of contrast agent particles can be calculated. If the concentration is constant, then relative variations in mean radius squared can be determined.

6 Claims, 11 Drawing Sheets

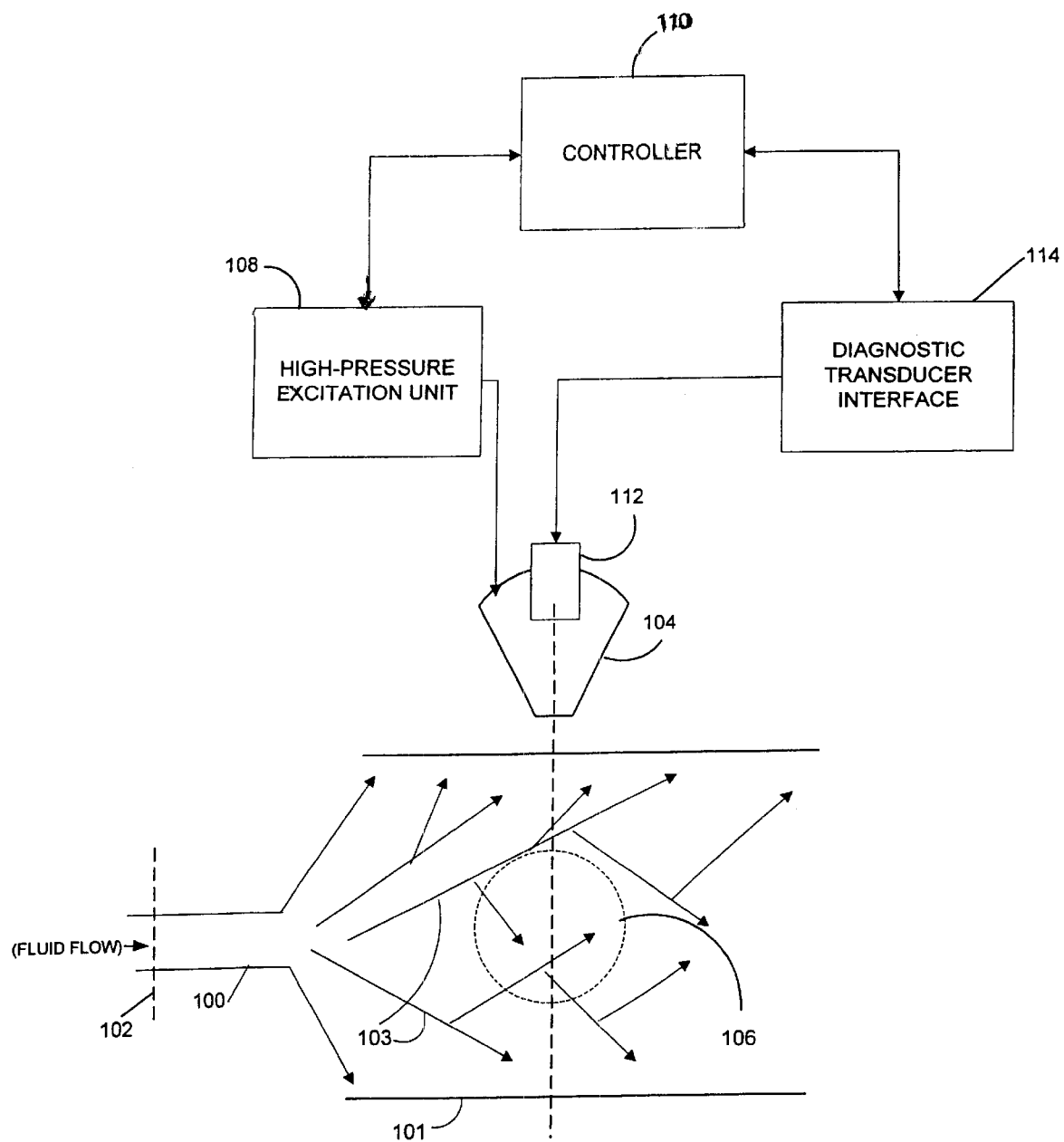

FIG. 2A
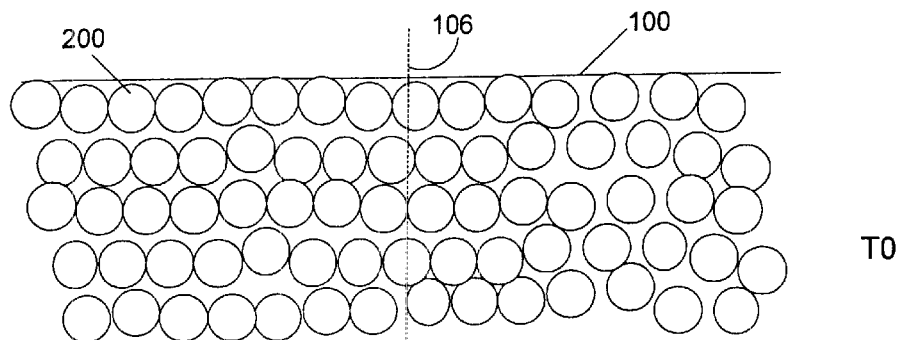
T0
FIG. 2B
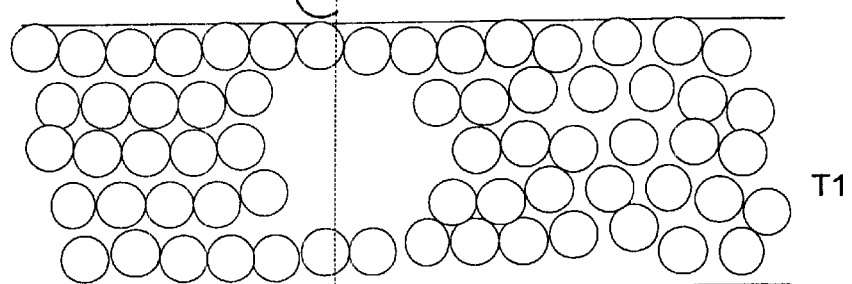
T1
FIG. 2C
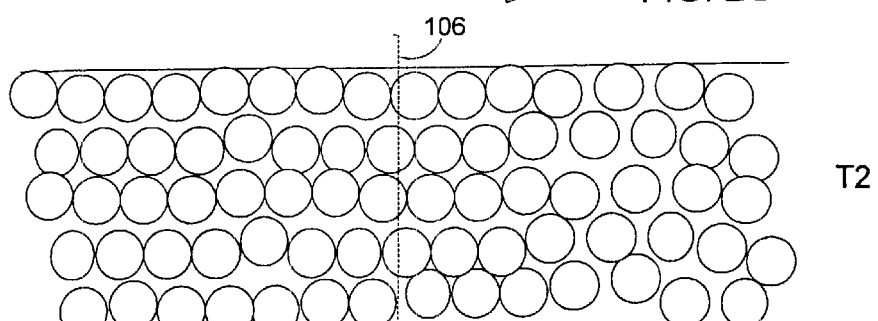
T2
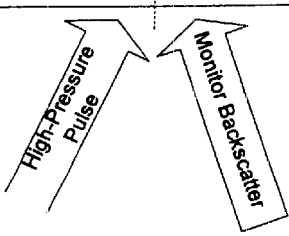

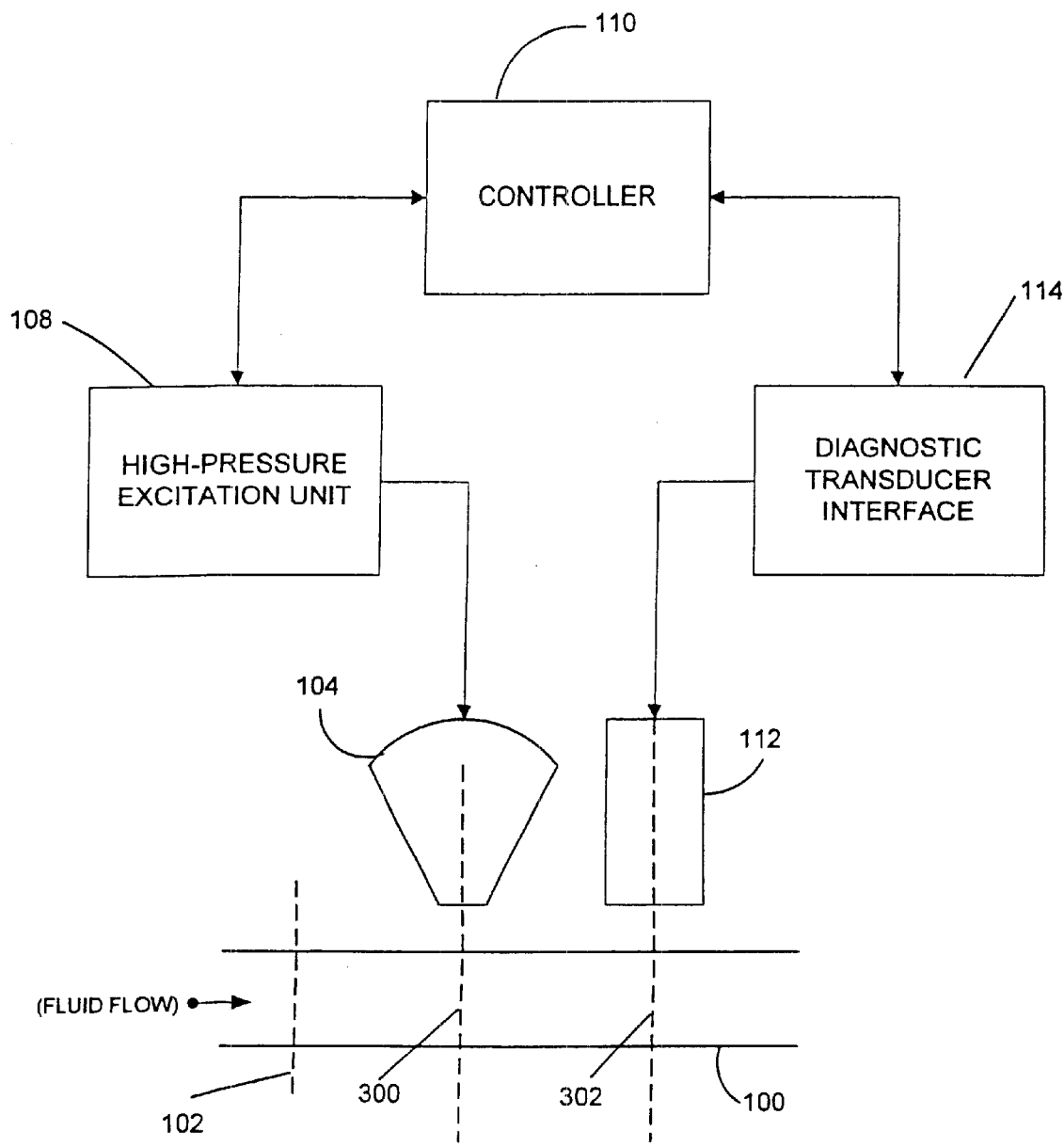

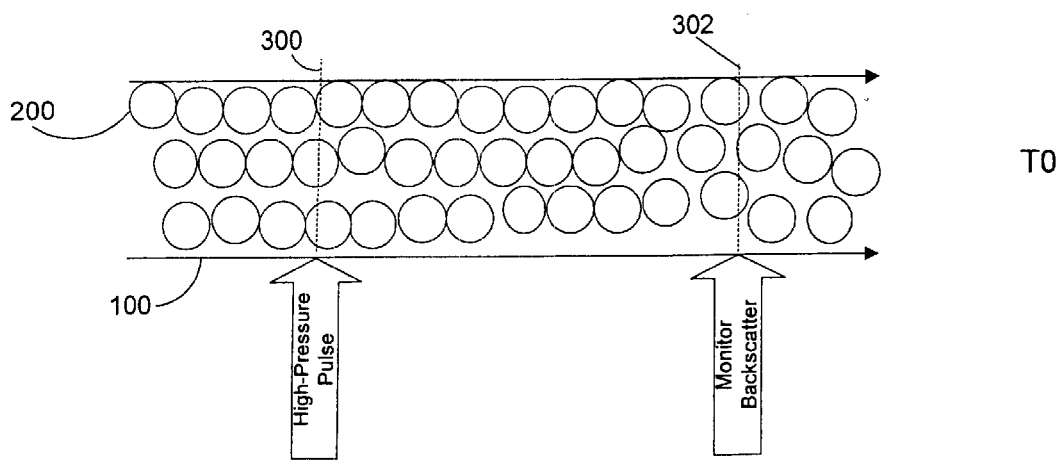
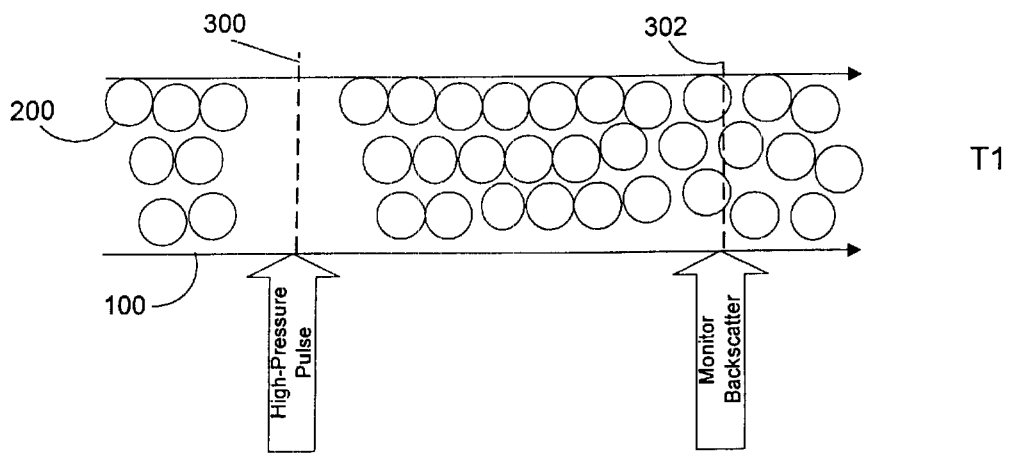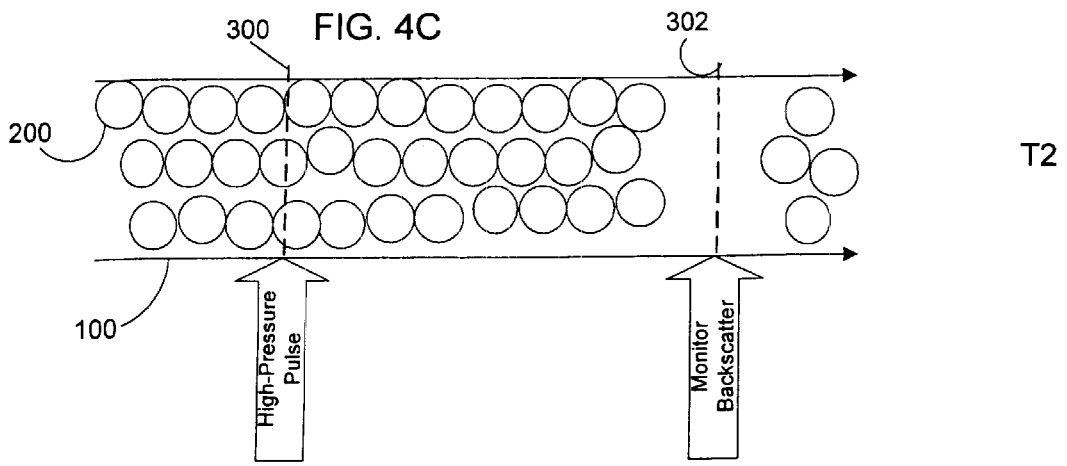

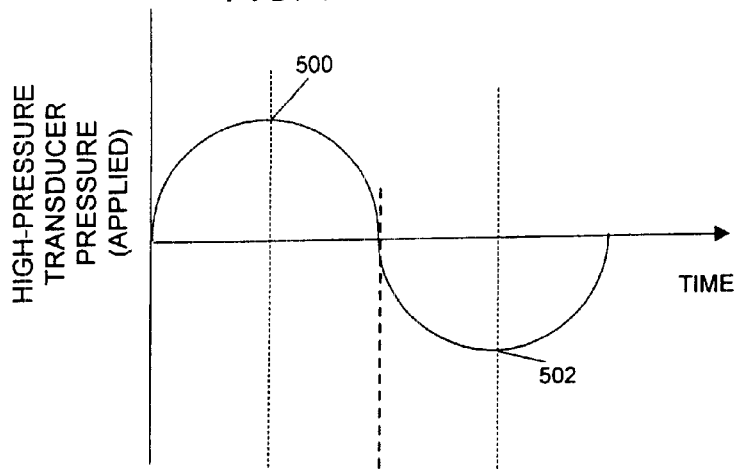
FIG. 5A
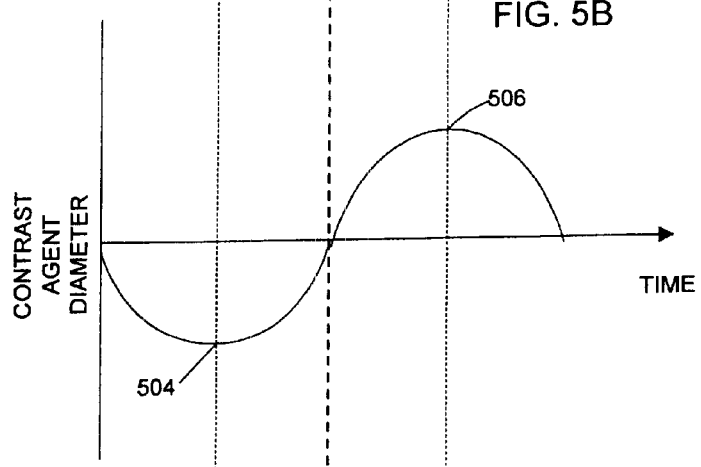
FIG. 5B
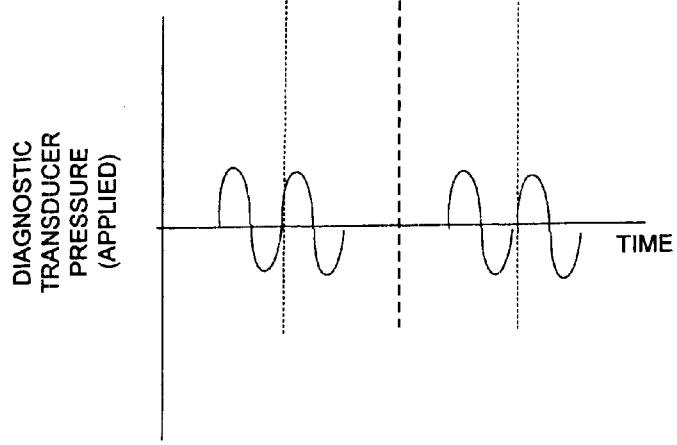
FIG. 5C
FIG. 5D

T0

T1

T2

ULTRASONIC SYSTEMS AND METHODS FOR CONTRAST AGENT CONCENTRATION MEASUREMENT

This application is a divisional application of Ser. No. 09/318,882 which was filed on May 26, 1999 now U.S. Pat. No. 6,186,951 entitled ULTRASONIC SYSTEMS AND METHODS FOR FLUID PERFUSION AND FLOW RATE MEASUREMENT, which claimed priority to U.S. Provisional patent application entitled Ultrasonic Contrast Methods for Perfusion Quantification, Ser. No. 60/086,748, which was filed on May 26, 1998.

FIELD OF THE INVENTION

The present invention relates generally to ultrasonic imaging, and more particularly relates to methods for measuring blood flow rate and perfusion employing ultrasound contrast agents.

BACKGROUND OF THE INVENTION

The accurate measurement of blood flow and blood perfusion is of great clinical importance for evaluating physiologic function and clinical conditions. Noninvasive Doppler sonography has been used to provide information on blood velocity and techniques have been developed to estimate volumetric blood flow rates from Doppler velocity measurements. Measurement of volumetric blood flow using traditional Doppler generally requires the determination of vessel size, beam/vessel angle and some estimate of the spatial variations in velocity. These requirements limit the accuracy of volumetric flow rate assessments because of the many sources of error in the velocity estimation using Doppler methods, such as errors in the estimation of vessel diameter and beam/vessel angle.

Ultrasonic contrast agents, which most commonly take the form of encapsulated gaseous micro-bubbles, which scatter ultrasound effectively, have been demonstrated to enhance ultrasonic images of blood and Doppler signals. With recent improvements in their ability to persist over longer periods of time, ultrasonic contrast agents hold great potential for improved blood flow and perfusion measurements in local tissue regions and organs. As their interactions with ultrasound are radically different from blood or soft tissue, the application of ultrasonic contrast agents opens new ground for developing new and better methods for quantification and characterization of fluid flow.

Ultrasound contrast agents can be used as blood volume contrast agents because they become distributed within the vascular space, travel at the same velocity as the blood flow rate or velocity, and remain relatively stable in the body during clinical observation periods. These characteristics provide the potential for mean flow rate estimation based on the indicator dilution principle using the contrast time-video intensity curve in ultrasonic images following a bolus injection. Such a process is described in the article "Mathematical Modeling of the Dilution Curves for Ultrasonic Contrast Agents," by C. M. Sehgal et al., J. Ultrasound Med., 16:471–479, 1997. However, current ultrasound methods that use the time-intensity curve in ultrasonic images following a bolus injection of a contrast medium are somewhat limited at present because 1) the interaction of ultrasound with contrast agents is not well understood; 2) the lack of knowledge of the number concentration of contrast agent and the rate of delivery, sometimes referred to as the "input function"; and 3) video intensity in ultrasonic images is a nonlinear conversion of returned echo amplitude from scatterers. Thus, improved methods of flow rate measurement using such contrast agents are required.

SUMMARY OF THE INVENTION

It is an object of the present invention to provide improved methods for determining the concentration of contrast agents in a fluid.

In accordance with the present invention, a method of determining the concentration of a contrast agent in a fluid in a region is provided which includes acquiring backscatter data from the region; extracting spectral parameters from the backscatter data; and estimating a contrast agent concentration using at least one spectral parameter and a predetermined distribution function for the contrast agent.

Preferably, the spectral parameter is derived from a linear regression of spectral data as a function of frequency.

Also in accordance with the invention, a method of calculating the function $C<r^2>$ is provided, where C is the concentration of contrast agent particles and $<r^2>$ is the mean of the radius squared of contrast agent particles in a region of a fluid. The method includes acquiring backscatter data from the region; extracting at least one spectral parameter from the RF backscatter data; and estimating the function $C<r^2>$ using the spectral parameters.

The methods described can be further enhanced by spectrum analysis procedures applied to radio-frequency (RF) echo signals (backscatter) received from contrast agent particles. The computed spectra can be analyzed with linear regression procedures to derive a spectral parameter, such as an intercept value, that is proportional to $C<r^2>$ where C is the concentration of contrast agent particles and $<r^2>$ is the mean value of their squared radii.

BRIEF DESCRIPTION OF THE DRAWING

Further objects, features and advantages of the invention will become apparent from the following detailed description taken in conjunction with the accompanying figures showing illustrative embodiments of the invention, in which FIG. 1 is a block diagram of an ultrasonic imaging system, suitable for practicing methods in accordance with the present invention;

FIGS. 2A–C are schematic diagrams pictorially illustrating a first method in accordance with the present invention;

FIG. 3 is a block diagram of an alternate embodiment of an ultrasonic imaging system, suitable for practicing methods in accordance with the present invention;

FIGS. 4A–C are schematic diagrams pictorially illustrating a method in accordance with the present invention.

FIGS. 5A–5D are related graphs illustrating the effect of an ultrasonic pressure wave on a contrast agent and an exemplary coherent relationship between a high-pressure ultrasound signal and a diagnostic ultrasound signal. In particular, FIG. 5A is a graph of high-pressure transducer output pressure versus time; FIG. 5B is a graph of contrast agent diameter versus time, coherent to FIG. 5A; FIG. 5C is a pictorial representation of contrast agent diameter versus time, coherent with FIG. 5A; and FIG. 5D is a graph of two applied diagnostic pressure pulses versus time, coherent with FIG. 5A.

Figure 6A:
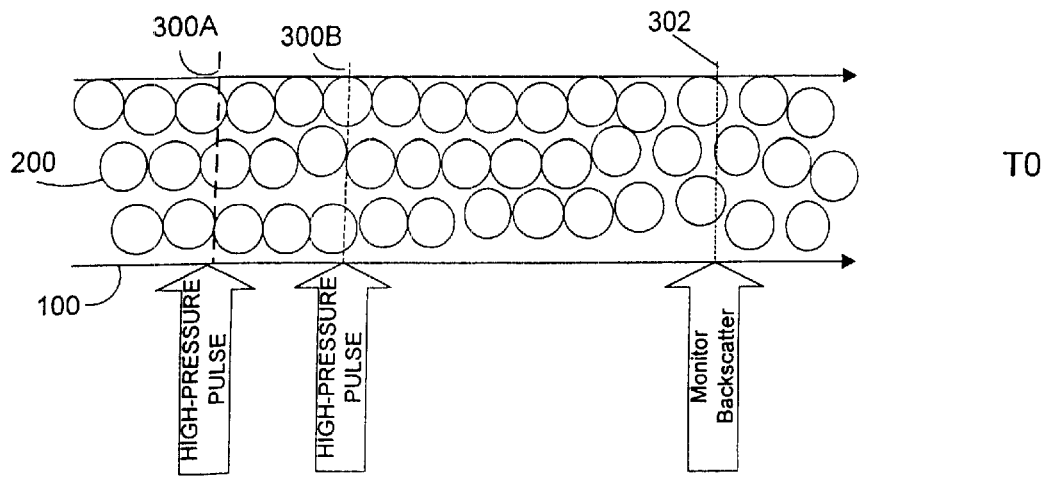
FIGS. 6A–C are schematic diagrams pictorially illustrating a method in accordance with the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

Ultrasonic imaging is an important and cost effective medical diagnostic tool. By introducing an ultrasonic contrast agent, the features of fluid-carrying tissue can be observed with enhanced clarity. In a present method, a contrast agent is introduced into a fluid stream, it is selectively eliminated or diminished by the application of a focused pulse of relatively low frequency ultrasonic energy and the restoration or movement of the region of diminished contrast agent is monitored, preferably using high frequency ultrasound, to determine the flow rate or perfusion rate of the fluid.

FIG. 1 illustrates a simplified block diagram of a system for performing a perfusion rate measurement method in accordance with the present invention. A fluid carrying conduit 100, such as an artery, is illustrated as supplying a fluid, such as blood, to a perfusion region 101. A contrast agent is introduced in the conduit 100 at an upstream location 102 such that the contrast agent is carried into and distributed throughout the region 101 by perfusion. Perfusion is achieved in tissue through a network of capillaries 103 distributed throughout the tissue. The ultrasonic contrast agent 200 generally takes the form of microbubbles whose physical properties, such as density and compressibility, differ substantially from those of the fluid and surrounding tissue, such that ultrasonic scattering is increased. While the conduit 100 is typically a vascular region, such as an artery, and the fluid being monitored is usually blood, the present methods are generally applicable to any fluid in any conduit. As such, the present systems and methods are applicable to monitoring industrial fluid transport systems as well as biological systems. While not limited to any particular contrast agent, Albunex®, manufactured Molecular Biosystems, Incorporated of San Diego, Calif., and Aerosomes (Definity), available from Dupont Pharmaceuticals, are suitable contrast agents for practicing the present methods. The presence and initial stable distribution of the contrast agent in the region 101 can be determined by low level ultrasound monitoring. FIG. 2A pictorially represents the region 101 in which a stable distribution of a contrast agent 200 has been achieved.

Ultrasound signals having a high peak pressure amplitude (hereinafter "high-pressure" ultrasound) has a destructive, and/or disruptive, effect on typical contrast agents which modifies the physical properties of the contrast agent. The contrast agents' microbubbles generally respond to a pressure wave in approximately an inverse relationship to the applied ultrasound pressure, as shown in FIGS. 5A–C. Further, when a pressure wave of sufficient amplitude is applied at a frequency near a resonant frequency of the microbubbles of the contrast agent 200, the microbubbles can be destroyed. Using this phenomenon as an advantage, a high-pressure transducer 104 is directed to a target position 106 in the region 101. The high-pressure transducer 104 is responsive to a high-pressure excitation unit 108 and controller 110, such that a defined pulse of focused ultrasonic energy in the form of a pressure wave can be delivered to the target position 106 within the region 101. The high-pressure transducer 104 generally emits a pulse of ultrasonic energy in the frequency range of 0.5–7 MHz, which is selected depending on the resonant frequency of the selected contrast agent. The effect of the pulse from the high-pressure transducer 104 is the modification or destruction of a large portion of the contrast agent 200 within the target position 106, as illustrated in FIG. 2B. While depicted in two dimensions, the zone of diminished backscatter which is created has a volume which can be estimated in vivo based on the depth of the target position 106, the power of the applied ultrasonic pulse, and the focal properties of the high-pressure transducer 104

The system of FIG. 1 also includes a diagnostic ultrasonic transducer assembly 112 which is similarly directed to the target region 106. This transducer assembly can include mechanical scan drives or an electronically controlled array to scan a diagnostic beam signal and form a cross-sectional scan image in a plane containing the beam from the transducer 104. In FIG. 1, the diagnostic ultrasonic transducer assembly 112 is shown as coaxially located with the high-pressure transducer 104. However, the two transducers can be adjacent and angularly directed to the common target position 106 or opposite one another and directed to the common target position 106. Alternatively, the operation of the high pressure transducer 104 and diagnostic transducer 112 can be provided for in a common assembly, such as a broadband ultrasound array. An ultrasound driver/processor 114 is operatively coupled to the diagnostic ultrasonic transducer assembly 112 and generates the ultrasonic driving signals therefor and receives RF backscatter signals therefrom under the control of controller 110. Preferably, the diagnostic ultrasonic transducer assembly 112 employs high frequency ultrasound to establish digitally generated B-mode image data. A commercially available system, such as the HDI Ultramark 9 available from ATL Ultrasound, Inc. of Bothell, Wash., is suitable for this operation.

By monitoring the target region 106 before, during and after the interval when contrast agent is depleted from a region, the time which is required for the contrast agent to return to its original level can be determined. This is illustrated as time $T_2$ in FIG. 2C. Further, since the volume of the contrast agent void can be readily estimated based on the expected in-situ power and focal properties of the pressure wave from the high-pressure transducer 104, the volumetric flow can also be determined. Alternatively, the volume of the zone of diminished backscatter can be estimated by evaluating ultrasound images of the zone using the diagnostic transducer assembly 112 before substantial replenishment of the contrast agent has occurred. Thus, the perfusion rate (volume of blood/time/tissue volume) can be ascertained.

The above described perfusion rate measurements can be performed using a dual-frequency band ultrasonic method which uses high-frequency pulses to monitor the alteration of contrast agent particles which result from the application of simultaneously applied low frequency ultrasound waves. This method combines the fine spatial resolution achievable at high center frequencies, such as 10 MHz, with the more pronounced contrast agent modifications that are caused at lower frequencies, near 1 MHz, which are closer to the contrast agents' resonant frequency. Such dual band methods also enhance the detectability of contrast agent particles at frequencies much higher than their resonant frequency, where their backscatter enhancement is generally relatively low.

Preferably, the dual-band method uses two beams that are coaxial or at least substantially coaxial. The high frequency pulse preferably occurs at a selected time/phase interval in the low frequency pulse; usually at intervals which are selected to occur near a low-frequency positive 500 or negative pressure peak 502. As illustrated in FIG. 5A through FIG. 5C, the contrast agent particles radii are minimum 504 and maximum 506, respectively at these temporal points. The backscatter measured with the high frequency pulse is correspondingly high (large particle radius) or low (small particle radius) at these respective phase relationships. As the contrast agent is modified to a greater extent than the surrounding tissue, only regions with contrast agents will exhibit significant backscatter changes associated with the low-frequency pressure. Thus, contrast agents can be sensed at high frequencies by comparing RF backscatter data taken on sequential low-frequency pulses where the high-frequency pulse is firstly provided at a positive pressure peak of the low frequency pulse and secondly provided at a negative pressure peak of the low frequency pulse. For example, the acquired RF backscatter data from these respective points can be aligned and subtracted, producing a non-negative result only from regions where contrast agent was present, thus enhancing the imaging capability of the ultrasound system. Such a method can be practiced using the apparatus of FIG. 1, where the controller 110 controls the time and phase of delivery of the signals to the high pressure transducer 104 and diagnostic transducer 114.

The dual band method can also be used in a second mode to sense the degree of contrast agent depletion produced by the low frequency pulse from the high pressure transducer 104. In this mode, a high-frequency pulse from the diagnostic transducer 112 occurs before the low frequency pulse, to establish an initial backscatter level in the region occupied by contrast agents as well as in distal regions whose backscatter echo signals are diminished because of the attenuation characteristic of contrast agents. A second high frequency pulse is launched from the diagnostic transducer 112 subsequent to the low frequency pulse and corresponding backscattered echo signals are compared to those from the first high-frequency pulse to determine alterations in contrast agent backscatter, caused by the preceding low frequency, high-pressure pulse. Alterations in the backscatter from distal tissues can also be examined to detect changes in intervening contrast-agent attenuation caused by modifications in contrast agents due to the low frequency pulse. The high-frequency pulse examination can be repeated at a series of time intervals following the low frequency pulse to monitor the temporal return of all backscatter levels to their initial values as new contrast agent particles enter the insonified region.

FIG. 3 illustrates an alternate embodiment of a system also in accordance with the present invention, which is particularly well suited for fluid flow rate (change in distance over change in time) measurements. The system is substantially similar to that described in connection with FIG. 1 except that the high-pressure transducer 104 is directed a first target zone 300 and the diagnostic transducer assembly 112 is directed to a second target zone 302, which is downstream from the first target zone 300. As with the system of FIG. 1, a contrast agent is injected into the fluid stream in conduit 100 at a location which is upstream of the high-pressure transducer 104, and is monitored to determine when a constant level of the contrast agent 200 is present, which is depicted as $T_0$ in FIG. 4A. At a time $T_1$, a pulse of ultrasonic energy is delivered by the high-pressure transducer 104 to the first target zone 300 in order to substantially reduce or modify the contrast agent 200 in a defined region of the fluid stream, as illustrated in FIG. 4B. The region where contrast-agent backscatter has been reduced provides reduced ultrasonic scattering and lower level return signals to the diagnostic transducer assembly 112. This region is referred to herein as a zone of reduced ultrasonic backscatter.

The fluid flowing past the second target region 302 is monitored by the diagnostic transducer assembly 112 to determine the time required (t) for the zone of reduced ultrasonic backscatter to flow into the second target region 302, as shown in FIG. 4C. Since the separation distance (d) between the high-pressure transducer 104 and diagnostic transducer assembly 112 is defined by the system setup, and therefore is known, once the time (t) that is required for the zone of reduced ultrasonic backscatter to traverse this separation distance is determined, the fluid flow rate, or velocity (V), can easily be determined by the equation, $V=d/t$.

In the foregoing methods and apparatus, reference has been made to the modification of physical parameters of the contrast agent in response to an applied high-pressure ultrasound signal. This modification generally takes the form of contrast agent destruction and/or contrast agent radius alteration. Referring to FIGS. 5A–5C, it is observed that in the presence of the low frequency ultrasonic pressure wave from the high-pressure transducer 104 the diameter of the microbubbles of the contrast agent 200 is not constant. Rather, the diameter varies in a substantially inverse relationship to the applied pressure wave, as is illustrated graphically in FIG. 5B and pictorially in FIG. 5C. Because the radii of the contrast agent particles varies over the cycle of the high-pressure signal, the backscatter of the contrast agent also varies. Thus, phase coherent operation of the high pressure transducer 104 and diagnostic transducer 112, as illustrated in the graph of FIG. 5D, is desired in some applications. This operation can be achieved in the apparatus of FIG. 1 since the controller 110 provides the driving signals for both the high pressure transducer 104 and diagnostic transducer 112. In addition, the substantially coaxial relationship of the high pressure transducer 104 and diagnostic transducer 112, as illustrated in FIG. 1, provides that the path length of the signals from the two transducers is substantially equal along the common signal beam path, thus providing for the coherent signal relationship to be maintained over a large target area.

Figure 6B:
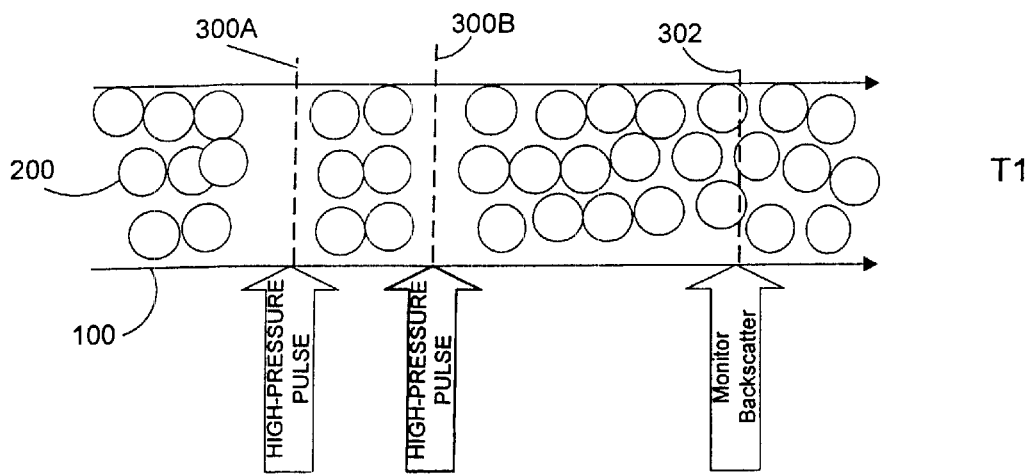
Figure 6C:
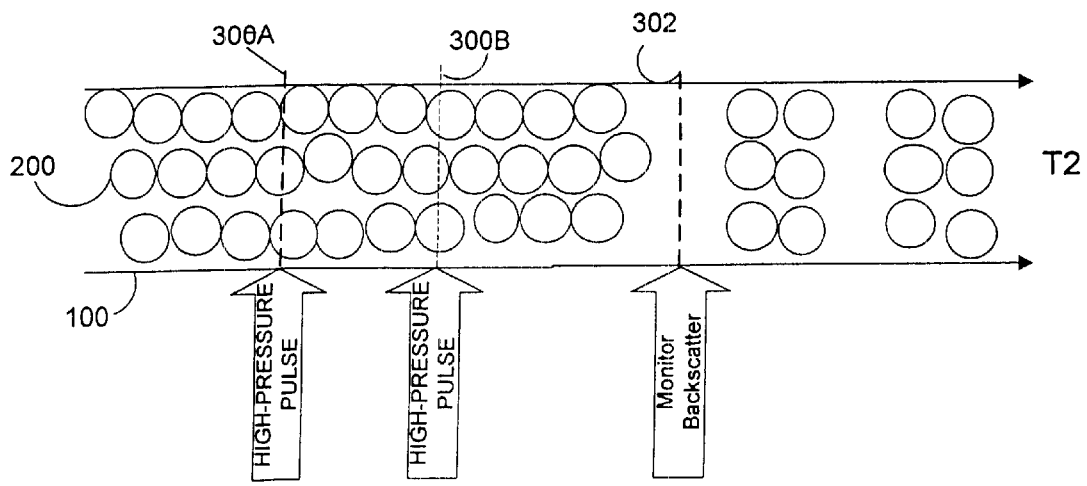

Since most conventional high-pressure transducers generally provide a single focal point, generally only a single zone of reduced ultrasonic backscatter is created in the fluid stream, as is illustrated in FIGS. 4A–C. However, certain known transducers can generate two or more simultaneous focal regions of high-pressure at predetermined positions, thereby creating two or more zones of reduced ultrasonic backscatter within the fluid stream. In this case, which is illustrated in FIGS. 6A–C, the distance between focal regions 300A and 300B is known. Therefore, by measuring the time that is required for both the first and second contrast agent zones of reduced ultrasonic backscatter to cross a given measurement point 302, the velocity of the fluid can be determined. This method has an advantage in that the separation between the first target regions 300A, 300B and second target region 300 need not be tightly controlled, as it is the spacing and time interval between consecutive regions of reduced ultrasonic backscatter generated at 300A and 300B which is being measured at point 300. As an alternate to using a transducer with simultaneous multiple focal regions, two or more high-pressure transducers spaced apart can be used.

Quantitative Backscatter Analysis

The methods and apparatus described in the preceding sections have generally employed an initial measured contrast level as a baseline for subsequent relative measurements following a contrast agent depletion operation. However, it is also possible to characterize and quantify the level of contrast agent in a region in absolute terms using the present invention. The following discussion sets forth the mathematical foundation for such quantitative analysis.

A useful starting point for analyzing contrast agent scattering is the Rayleigh-Plesset-Noltingk-Neppriras-Poritsky (RPNNP) equation, set forth in the article "Numerical Studies of the Spectrum of Low-Intensity Ultrasound Scattered by Bubbles" by B. C. Eatock et al. J. Accoust. Soc. Am. 77:1672–1701; 1985, which describes the radial motion of a free spherical bubble in a liquid driven by a sound field as:

$$\rho_0 R \frac{d^2 R}{dt^2} + \frac{3}{2}\rho_0 \left(\frac{dR}{dt}\right)^2 = P_{go}\left(\frac{R_0}{R}\right)^{3\Gamma} + P_v - P_a - \frac{2\sigma'}{R} - 2\pi f \delta \rho_0 R \frac{dR}{dt} - p(t), \quad (1)$$

where $\rho_0$ is the density of the surrounding medium, R is the radius of the bubble at time t, $R_0$ the initial radius, $P_{go}$ the initial gas pressure inside the bubble, $\Gamma$ the polytropic exponent of gas, $P_a$ the ambient pressure, $\sigma'$ the surface tension coefficient, p(t) the time-varying acoustic pressure, f the frequency of the incident acoustic field, and $\delta$ the total damping coefficient. A Rayleigh-Plesset like equation has been developed by C. Church for an encapsulated bubble (such as Albunex) by incorporating the effects of a thin elastic solid layer, as described in "The Effects of an Elastic Solid Surface Layer on the Radial Pulsations of Gas Bubbles," J. Acount. Soc. Am. 97:1510–1521, 1995 (hereinafter, "Church"). This reference derives an analytical solution of the equation for relatively low-pressure amplitudes by using a perturbation method and assuming a summation of harmonics as the solution.

Using Church's definition for the scattering cross section for a bubble of radius R, $$\sigma(f,R) = 4\pi r^2 |p_s|^2/|p|^2, \quad (2)$$

where $p_s$ is the scattered pressure which can be computed from R(t), the solution of the bubble dynamics equation (eq. 1). The total scattering cross section of a collection of bubbles is proportional to the concentration of bubbles (number of particles per unit volume), when the interaction among bubbles can be ignored. The calibrated spectrum analysis method discussed below incorporates the scattering cross section obtained from the bubble dynamics equation.

First, consider the calibrated complex spectrum $S_m$ of radio frequency (rf) echoes from a range-gated contrast-agent region of length L. The range gate is located at a range r in the focal volume of a transducer with aperture radius $\alpha$ and focal length equal to r. This spectrum is computed by multiplying the RF signals with a Hamming function and performing a Fast Fourier Transform (FFT). The resulting spectrum is divided by a calibration spectrum derived from a planar reflective surface (e.g., of an optically flat glass plate in a water tank in the transducer's focal plane). This calibration procedure removes the spectrum of the launched pulse from the measurement. Under the above conditions, the spectrum is found to involve a convolution (*) with the spectrum of the gating function $S_G$ $$S_m(f, R) \approx s_G(k) * \frac{a^2}{4\sqrt{\pi}} \sqrt{\sigma(f, R)} \frac{e^{-j2kr}}{r^2} \int C(\vec{x}) F^2(y, z) d\vec{x}, \quad (3)$$

where the wave-number k=2πf/c, f is temporal frequency, c is the propagation velocity in the surrounding fluid, and $\vec{x}$ is a spatial coordinate vector (x is the axial propagation coordinate, y and z are cross-range coordinates). $\sigma(f,R)$ is the frequency-dependent scattering coefficient of a single contrast agent particle of radius R. The concentration function $C(\vec{x})$ includes a collection of delta functions which describe the random location of each contrast agent particle of radius R. $F^2$ is the two-way beam directivity function $[2J_1(k\alpha\sin\theta)/(k\alpha\sin\theta)]^2$ where $\sin\theta = (z^2+y^2)^{1/2}/r$ and $J_1()$ denotes a Bessel function of the 1st kind and 1st order.

Because contrast agent particles are spatially distributed in a random manner, $C(\vec{x})$ is a stochastic function and $S_m$, set forth in equation 3, represents a single realization of the backscatter. The average calibrated power spectrum is then computed by averaging M independent measurements of $|S_m|^2$. Independent measurements can be obtained along adjacent scan lines (separated by a beam-width) or by single-line measurements obtained at temporal intervals that permit new groups of contrast agents to enter the beam. This average power spectrum is an estimate of the "true" ensemble power spectrum $S = \overline{S_m S^*_m}$ where $S^*_m$ is the complex conjugate of $S_m$ and the superscript bar denotes expected value.

The ensemble average power spectrum S is computed as:

$$S(f, R) = \frac{a^4 \sigma(f, R)}{16\pi r^4} k^2 \int R_C(\Delta\vec{x}) R_{F^2}(\Delta y, \Delta z) e^{-j2k\Delta x} d\Delta \vec{x} * \int R_G(\Delta x) e^{-j2k\Delta x} d\Delta \vec{x} \quad (4)$$

where $\Delta \vec{x}$ denotes lagged spatial coordinates $\Delta x$, $\Delta y$, and $\Delta z$; $R_c$ is the spatial auto-correlation function (ACF) of the concentration function $C(\vec{x})$; $R_F^2$ is the cross-range ACF of the beam directivity function $F^2$ and $R_G$ the axial ACF of the gating function.

For contrast agent particles with independent, uniformly random positions, the concentration function ACF is $$R_C(\Delta\vec{x}) = \bar{C}\delta(\Delta\vec{x}) + \bar{C}^2, \quad (5)$$

where $\bar{C}$ is the average concentration (number of particles per unit volume) of particles of radius R and $\delta(\Delta\vec{x})$ denotes the product of delta functions $\delta(\Delta x)$, $\delta(\Delta y)$, and $\delta(\Delta z)$. The directivity function ACF is approximately a Gaussian function of $(\Delta y^2 + \Delta z^2)$ with $$R_{F2}(0,0) \approx 0.361 \frac{4\pi r^2}{k^2 a^2}.$$

The gating function ACF depends on the gating function; for a Hamming function of length L, $R_G(0)=0.4L$. We treat the case in which L is large so that the bandwidth of the second integral in eq. 4 is much smaller than the bandwidth of the first integral, $$S(f, R) = \frac{k^2 a^4}{16\pi r^4} \overline{C}\sigma(f, R) R_{F2}(0,0) R_G(0) \quad (6)$$

$$= 0.036 \overline{C}\sigma(f, R) \frac{a^2 L}{r^2}.$$

Equation 6 shows that the calibrated spectra of contrast particles of radius R are related to the scattering cross section of a single particle multiplied by the number of particles of that radius and factors associated with the transducer (i.e., aperture radius $\alpha$, range/focal length r), and the analysis gate (L). We also obtain similar results for the focal volumes of rectangular phased arrays.

A normalized size-distribution function n(R) ($\int n(R)dR = 1$) is employed to describe contrast agent suspensions containing independent particles with different radii. The total contrast-agent particle concentration is $\overline{C}_T$, and, $\overline{C} = \overline{C}_T n(R)dR$ represents the number of particles of radius between R and R+dR within a unit volume. Therefore, for contrast agent suspensions containing independent particles with different radii, the calibrated power spectrum is equal to the weighted sum of constituent power spectra computed from equation 6 for particles of each radius, $$S(f) = 0.036 \frac{a^2 L}{r^2} \overline{C}_T \int \sigma(f, R) n(R) dR. \quad (7)$$

Useful summary spectral parameters can be derived by 1) expressing calibrated spectra (equation 7) in dB and 2) computing linear regression parameters over the useable bandwidth. This approach can be used to derive spectral intercept (dB, extrapolation to zero frequency) and spectral slope (dB/MHz). Such techniques are discussed in further detail in commonly assigned U.S. Pat. No. 4,858,124 to Lizzi et al., which is expressly incorporated herein by reference. The calibrated power spectrum can be expressed in dB as $$S_{db}(f) = 10 \log\left(0.036 \frac{a^2 L}{r^2}\right) + 10 \log(\overline{C}_T) + 10 \log\left(\int \sigma(f, R) n(R) dR\right). \quad (8)$$

Applying a linear regression to equation 8 and noting that the linear regression operators for intercept, INT(·), and slope, SLP(·), are linear. The result for the linear fit is:

$$S_{db}(f) \cong I_1 + I_2 + I_3 + m \cdot f, \quad (9)$$

where the intercept I consists of three terms:

$$I_1 = 10 \log\left(0.036 \frac{a^2 L}{r^2}\right),$$

$I_2 = 10 \log(\overline{C}_T)$, and $I_3 = \text{INT}[10 \log(\int \sigma(f,R) n(R) dR)]$. The slope $m = \text{SLP}[10 \log(\int \sigma(f,R) n(R) dR)]$. The intercept components are related to known system constants ($I_1$), total particle concentration ($I_2$), and the weighted-average scattering cross-section ($I_3$) which also determines the slope m. In addition, $I_3$ and m of the linear fit also depend on the frequency band being analyzed.

The above results show that $I_2$ is the only term affected by $\overline{C}_T$. Thus, the intercept is related in a simple fashion to the total concentration $\overline{C}_T$ and, as discussed below, can be used to estimate $\overline{C}_T$. The slope is independent of $\overline{C}_T$ and system parameters, and is affected only by the frequency-dependent scattering of contrast agent particles and their radius distribution.

The following section presents spectral intercept and slope computed for an exemplary Albunex® contrast agent, over several frequency ranges. These values are calculated without intervening attenuation effects. If intervening attenuation is present it will multiply calculated values of S by $\exp(-\beta r)$. Typically, the effective tissue attenuation coefficient $\beta$(nepers/cm) is approximately linearly proportional to frequency. In this case, the measured power spectrum (in dB) will exhibit a linear fit S' equal to $$S' = I + mf - 2\alpha' f r = I + (m - 2\alpha' r) f, \quad (10)$$

where the attenuation coefficient $\alpha'$ is now expressed in dB/MHz/cm. Thus, attenuation lowers the measured slope by a factor of 2 $\alpha' r$ (dB/MHz) but, most importantly, it does not affect the spectral intercept I. Thus, unlike other backscatter parameters, results for intercept are independent of attenuation in intervening tissue.

Church's theoretical formulation for the scattering cross section $\sigma(f, R)$ and shell parameters reported for Albunex®, is used to evaluate calibrated power spectra and spectral parameters for Albunex®. Results were obtained for Albunex® populations with a single radius or a distribution of radii over the relevant frequency band.

Albunex® particles with a single radius $\overline{R}$ are analyzed by substituting $n(R) = \delta(R-\overline{R})$ into equation 8, where $\delta$ represents Kronecker delta function, and obtaining the calibrated spectrum as $$S_{db}(f) = 10 \log\left(0.036 \frac{a^2 L}{r^2}\right) + 10 \log(\overline{C}_T) + 10 \log[\sigma(f, \overline{R})]. \quad (11)$$

Figure 7:
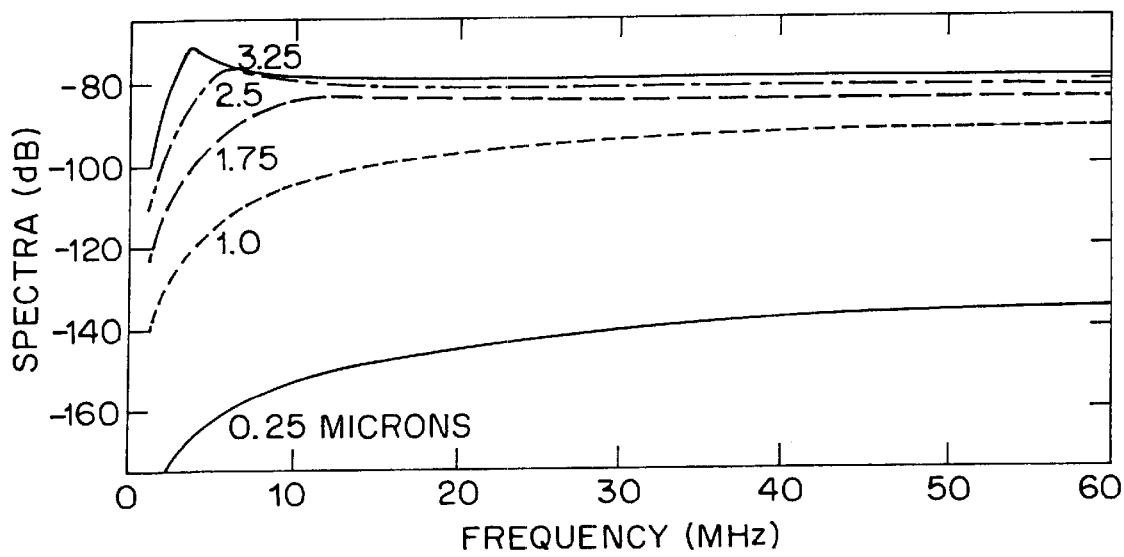
FIG. 7 is a graph of calibrated power spectra for an exemplary contrast agent, Albunex®, with various radii.

From this equation, spectra over a frequency range of 1 MHz to 60 MHz can be computed for Albunex® particles of different radii (from 0.5 to 3.25 $\mu$m, and $k\overline{R} < 1$ for the frequency range); we included the parameters of our Very High Frequency Ultrasound (VHFU) system used in our experiments ($\alpha = 0.3$ cm, r=1.2 cm, L=0.03 cm). We also set $\overline{C}_T = 1/\text{cm}^3$ ($I_2 = 0$). (A change of concentration will affect only the spectral magnitude, not the spectral shape or slope.) Results are shown in FIG. 7. The spectra initially rise rapidly with frequency, and some (for larger radii, e.g. 3.25 $\mu$m) exhibit resonance peaks below 10 MHz before leveling off at higher frequencies. At these higher frequencies, the spectra approach frequency-independent constants for all analyzed radii, a fact indicating that the scattering cross-section $\sigma(f,\overline{R})$ depends only on radius, not frequency, at these high frequencies.

Figure 8A:
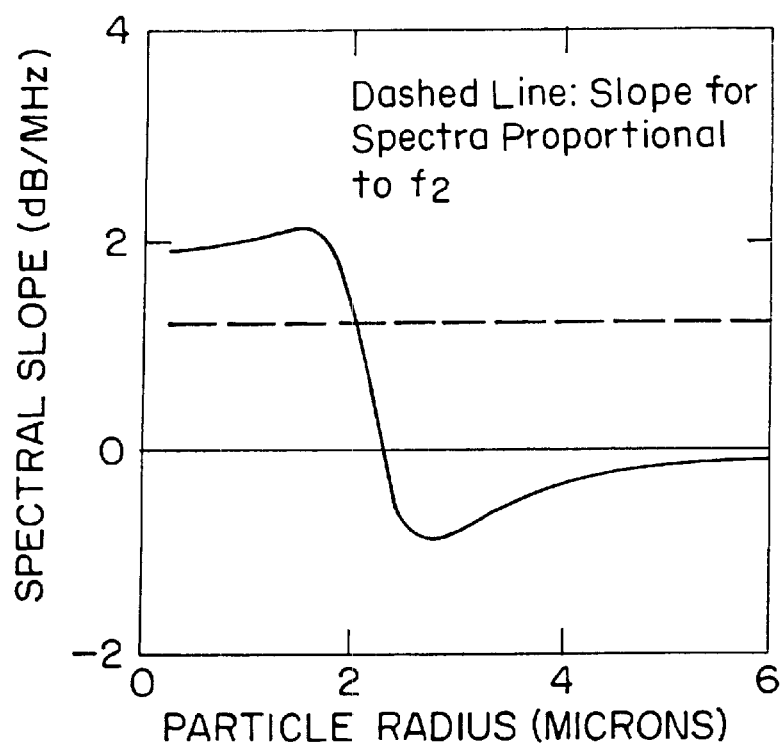
FIGS. 8A and 8B are graphs of spectral slope and intercept value, respectively, versus contrast agent (Albunex®) particles over a frequency of 5.5 to 9.0 MHz.
Figure 8B:
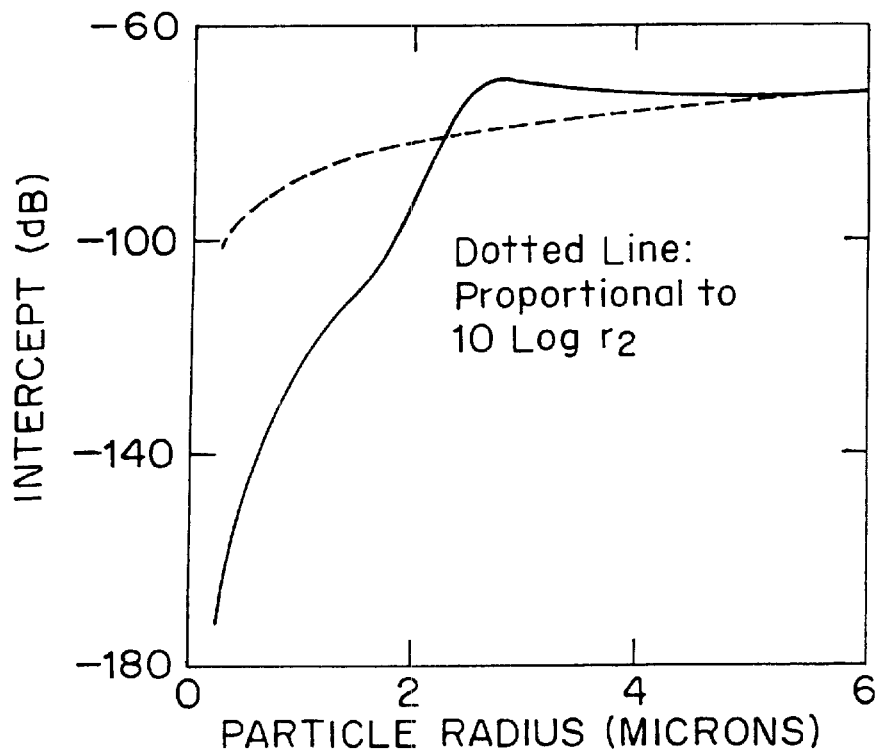
Figure 9A:
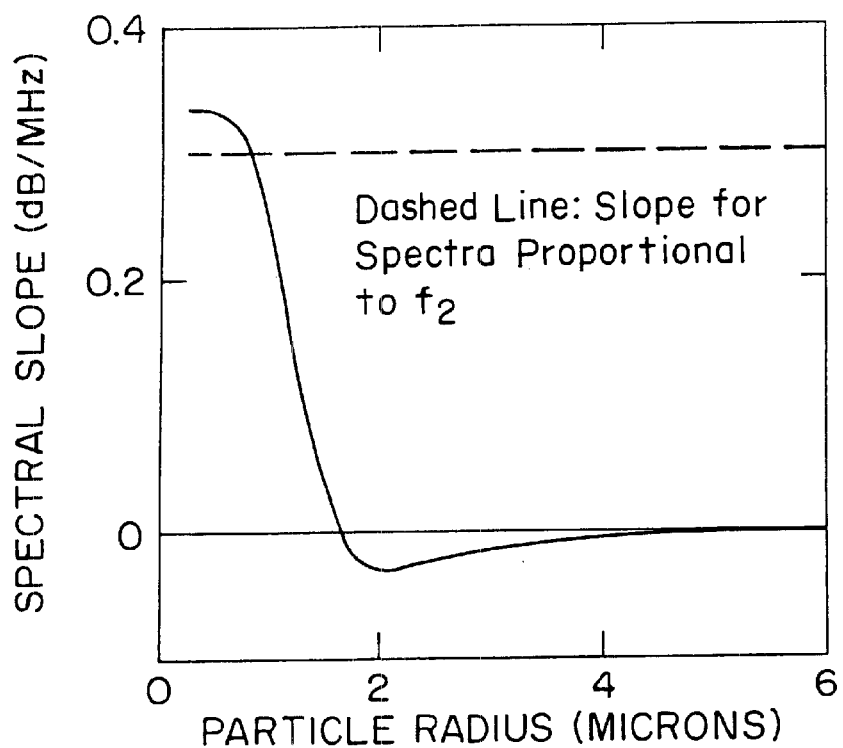
FIGS. 9A and 9B are graphs of spectral slope and intercept value, respectively, versus contrast agent (Albunex®) particles over a frequency of 10 to 55 MHz.
Figure 9B:
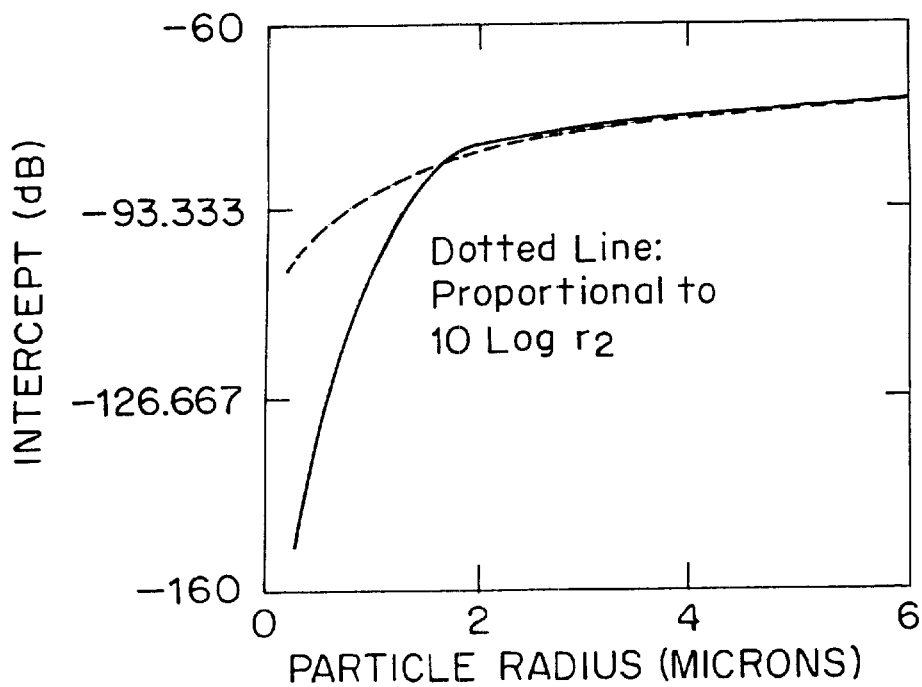
Figure 10A:
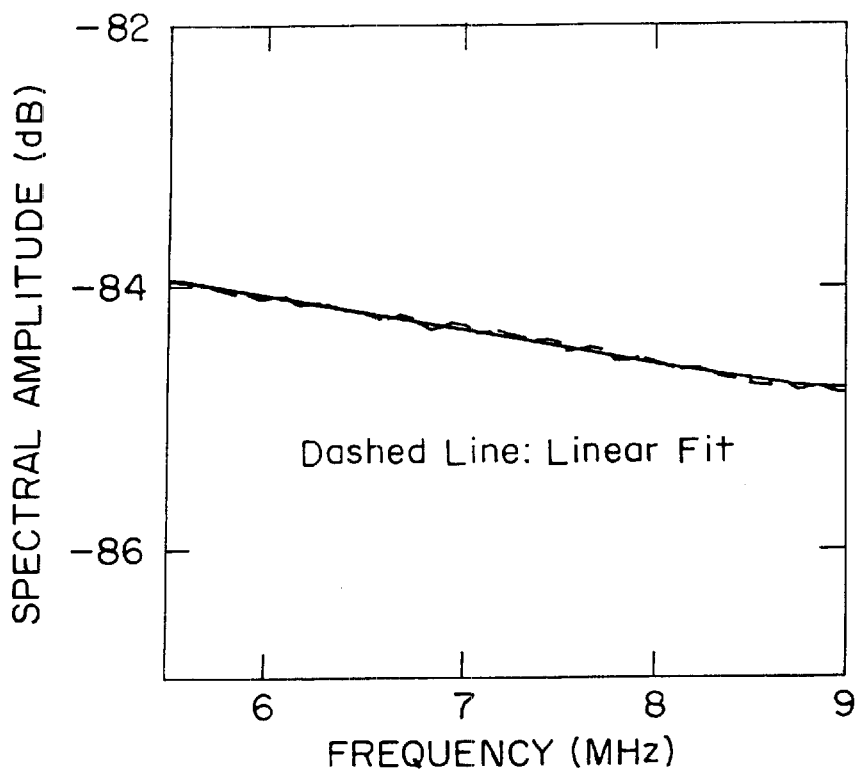
FIGS. 10A and 10B are graphs of theoretical spectral amplitude in decibels versus frequency for polydisperse Albunex particles over frequency ranges of 5.5–9.0 MHz and 10 to 55 MHz, respectively.
Figure 10B:
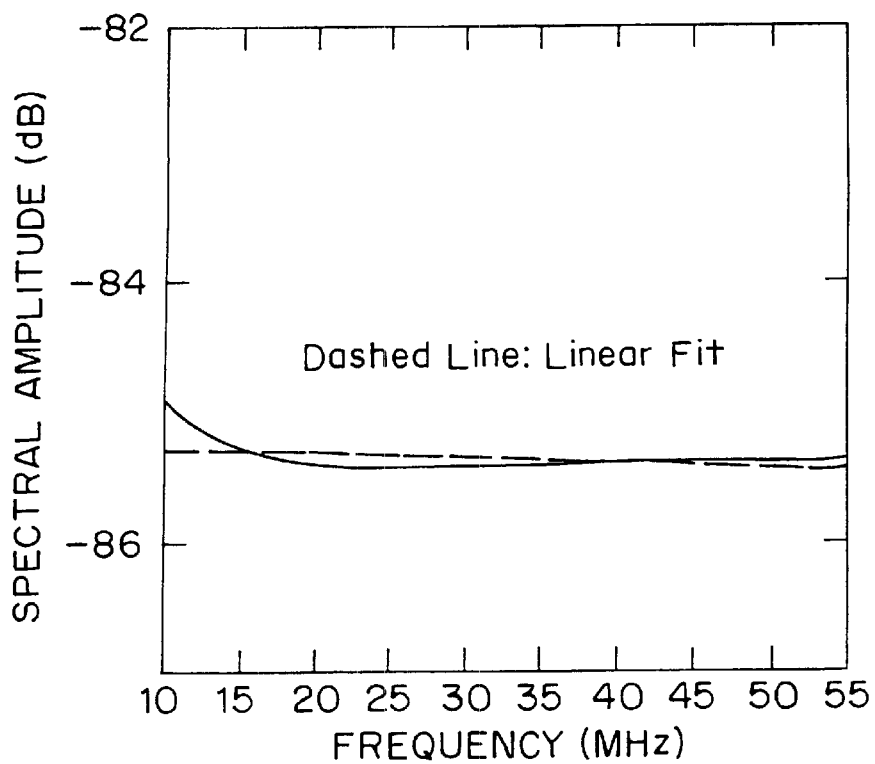

The calculation of spectral parameters, requires selection of several representative bandwidths, computed linear fits to spectra in dB, and derived plots of spectral slope and intercept versus. particle radius. FIGS. 8A and 8B show the results for the 5.5 to 9.0 MHz band (relevant to data acquired using the ATL HDI ultrasound system). Note that spectral slope changes abruptly from 2dB/MHz to negative values as particle radius becomes larger than 2 μm. For radii larger than about 2 μm, intercept varies as 10 log($\bar{R}^2$), as indicated by the dotted line. FIGS. 9A and 9B show results for the 10 to 55 MHz band. For radii larger than about 1.5 μm, spectral slope is relatively constant (near zero) and intercept is proportional to 10log($\bar{R}^2$). Using equation (9), we found that, for VHFU frequencies, $$\sigma(f,\bar{R}) \approx 4\pi\bar{R}^2 \text{ for } \bar{R} \geq 1.5 \ \mu m, \quad (12)$$

indicating that the scattering cross-section of reasonable large contrast agent particles depends only on radius at VHFU frequencies.

Spectra were also computed for each frequency band in the distribution of a range of Albunex® particle sizes. Results of these spectral computations are plotted in FIG. 9, along with linear regression fits for a total concentration of $1 \times 10^7/cm^3$. The calibrated power spectrum is the weighted average of the spectra of contrast agent particles of all radii; therefore, as expected, the resulting spectrum is fairly flat over our VHFU frequency band. The size distribution affects the intercept but does not significantly affect the slope over this frequency band.

FIGS. 8A, 8B and 9A, 9B can be used in practice to extract concentration information assuming that all Albunex® particles have the same radius. For poly-disperse Albunex® particles with known particle size distribution, the concentration can be estimated by matching the theoretical results of slope and intercept with measured results. Further, the intercept depends strongly on $\bar{C}_T \bar{R}^2$, a fact indicating that the details of the distribution function n(R) might not be so important; as described next, we found that we can treat different distribution functions in simple terms to obtain estimation of concentration information.

Figure 11:
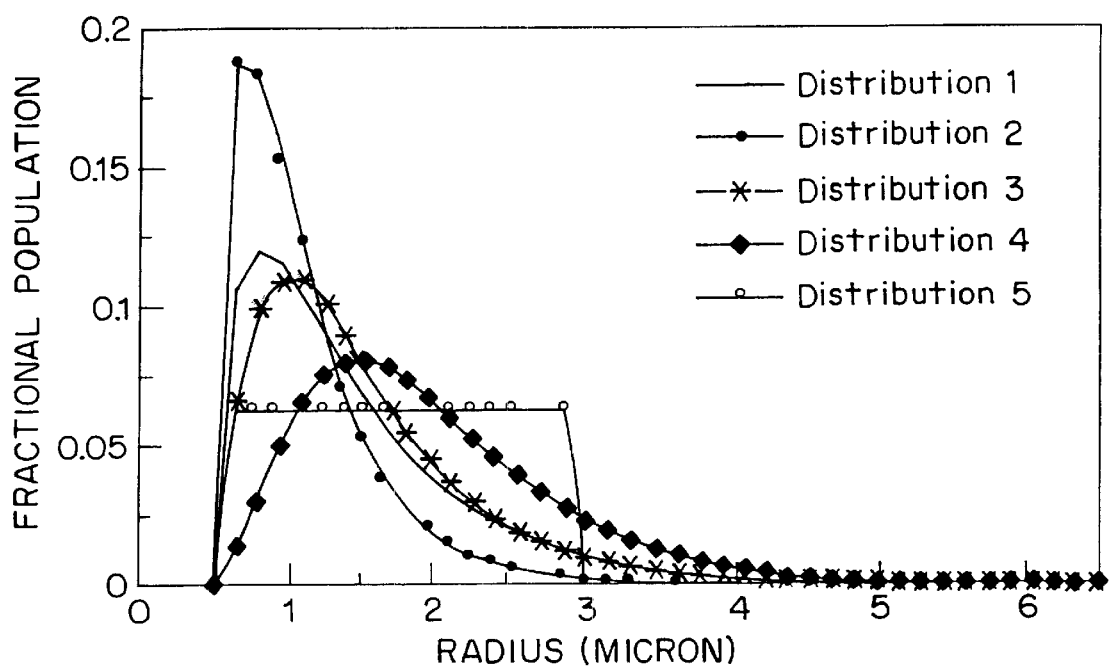
FIG. 11 is a histogram graph of normalized size distributions versus particle radius.

A Γ-distribution function is used to represent the normalized size distribution of Albunex® particles $$n(R) = \begin{cases} A(R-R_0)^{\alpha-1} e^{-\beta(R-R_0)} & R > R_0 \\ 0 & R \leq R_0, \end{cases} \quad (13)$$

where α, β, and $R_0$ are parameters determining the shape of the function, and A is a normalizing constant for the distribution. This function closely matches the distribution measured by Church when $R_0=0.5$ μm, α=1.5, and β=0.8/$R_0$. Different size distributions are examined by varying parameters α and β while keeping $R_0$ at 0.5 μm. FIG. 11 illustrates the Γ-distributions we considered as well as a uniform distribution function (from 0.5 to 3 μm). A calibrated power spectra is calculated for these distribution functions with a total concentration of $5 \times 10^7/cm^3$ and our VHFU parameters ($I_1+I_2=35.3$ dB). For comparison, we also calculate approximate intercept, using equation 12, as $$\tilde{I}=I_1+10 \log (\bar{C}_T)+10 \log(4\pi<R^2<), \quad (14)$$

where $<R^2>$ is the mean square radius computed from the size distribution. Results are summarized in Table 1. Comparing I with $\tilde{I}$ in Table 1, it is seen that equation 12 is a very good approximation (to within about 1 dB) for the scattering cross section. The spectral slope and intercept are not sensitive to the details of size distribution over this frequency range and the intercept is affected primarily by the mean square radius $<R^2>$.

TABLE 1

Distributions and spectral results

| Γ-functions | $<R>(\mu m)$ | $<R^2>(\mu m^2)$ | Slope (dB/MHz) | I(dB) | $\tilde{I}$(dB) | I-$\tilde{I}$(dB) |
|---|---|---|---|---|---|---|
| 1: α = 1.5, β = 0.8/$R_0$ | 1.45 | 2.72 | $8 \times 10^{-4}$ | −29.7 | −29.4 | −0.3 |
| 2: α = 1.5, β = 1.3/$R_0$ | 1.10 | 1.51 | 0.021 | −33.7 | −32.0 | −1.7 |
| 3: α = 2, β = 1/$R_0$ | 1.50 | 2.77 | $3 \times 10^{-4}$ | −29.6 | −29.3 | −0.3 |
| 4: α = 3, β = 1/$R_0$ | 2.00 | 4.75 | −0.008 | −26.6 | −27.0 | 0.4 |
| 5: uniform, 0.5~3 μm | 1.75 | 3.42 | −0.01 | −28.0 | −26.9 | −1.1 |

Thus, the absolute value of $\bar{C}_T<R^2>$ is estimated to within about 1 dB from intercept even for such different distribution functions. Thus, the value of $\bar{C}_T<R^2>$ is a suitable measure of "effective concentration," which can be used for flow, volume and perfusion estimation.

The above-described quantitative backscatter analysis techniques can be used to estimate the concentration of contrast agent in a region. This method can be used in any application where a concentration estimate is desired, including use in conjunction with the flow rate and perfusion rate techniques previously described.

As set forth herein, the present invention provides apparatus and methods for performing perfusion rate measurements using ultrasound techniques by introducing a contrast agent into a region, depleting the contrast agent from a known volume of the region using a destructive pulse of ultrasound energy, and then monitoring the recovery of the contrast agent within the region using non-destructive ultrasound energy.

The present invention also provides apparatus and methods for performing flow rate measurements of a fluid in a conduit using ultrasound techniques by introducing a contrast agent into an upstream location of the conduit, depleting the contrast agent from a first downstream location in the conduit using a pulse of ultrasound energy to create a zone of reduced ultrasonic backscatter in the fluid stream, and then monitoring a second downstream location to detect the arrival of the zone of reduced ultrasonic backscatter using non-destructive ultrasound energy.

It is also an aspect of the present invention that first and second ultrasound transducers are operated in a phase coherent manner such that a predetermined phase relationship in the signals provided by the transducers is maintained. By maintaining a predetermined phase relationship, improved contrast agent measurements can be performed.

The concentration and/or radii of a contrast agent in a fluid can also be determined using ultrasound apparatus and methods in accordance with the present invention. By acquiring ultrasound spectral data, performing spectral analysis to generate a linear estimation of the power spectrum, and correlating at least one spectral parameter to a predetermined distribution function for the contrast agent, effective concentration levels can be estimated. If the mean radius squared of particles is known, then the concentration of contrast agent particles can be calculated. If the concentration is constant, then relative variations in mean radius squared can be determined.

Although the present invention has been described in connection with specific exemplary embodiments, it should be understood that various changes, substitutions and alterations can be made to the disclosed embodiments without departing from the spirit and scope of the invention as set forth in the appended claims.

What is claimed is:

1. A method of determining the concentration of a contrast agent in a fluid in a region comprising:

acquiring radio frequency backscatter data from the region;

extracting spectral parameters from the radio frequency backscatter data; and estimating a contrast agent concentration using at least one spectral parameter and a predetermined distribution function for the contrast agent.

2. The method of determining the concentration of a contrast agent in a fluid in a region as defined by claim 1, wherein the at least one spectral parameter is derived from a linear regression of spectral data as a function of frequency.

3. The method of determining the concentration of a contrast agent in a fluid in a region as defined by claim 1, further comprising the step of providing a visual indication of said concentration estimation.

4. A method of calculating the function $C<r^2>$, where C is the concentration of contrast agent particles and $<r^2>$ is the mean of the radius squared of contrast agent particles in a region of a fluid, comprising:

acquiring radio frequency (RF) backscatter data from the region;

extracting at least one spectral parameter from the RF backscatter data; and estimating the function $C<r^2>$ using the spectral parameters.

5. The method as defined by claim 4, wherein the at least one spectral parameter is derived from a linear regression analysis of the backscatter data as a function of frequency.

6. The method as defined by claim 4 further comprising the step of providing a visual indication of the estimated function $C<r^2>$.

* * * * *